US012758909B2

(12) United States Patent
Thompson

(10) Patent No.: US 12,758,909 B2
(45) Date of Patent: Oct. 13, 2026

(54) FAN COVER

(71) Applicant: Aijah Thompson, Federal Way, WA (US)

(72) Inventor: Aijah Thompson, Federal Way, WA (US)

( * ) Notice: Subject to any disclaimer, the term of this patent is extended or adjusted under 35 U.S.C. 154(b) by 319 days.

(21) Appl. No.: 18/669,338

(22) Filed: May 20, 2024

(65) Prior Publication Data

US 2024/0382888 A1 Nov. 21, 2024

Related U.S. Application Data

(60) Provisional application No. 63/503,085, filed on May 18, 2023.

(51) Int. Cl.

| | |
|---|---|
| ***B01D 46/02*** | (2006.01) |
| ***A61L 9/014*** | (2006.01) |
| ***A61L 9/12*** | (2006.01) |
| ***B01D 46/00*** | (2022.01) |

(52) U.S. Cl.

CPC .............. *B01D 46/02* (2013.01); *A61L 9/014* (2013.01); *A61L 9/12* (2013.01); *B01D 46/0028* (2013.01); *B01D 46/0038* (2013.01); *B01D 46/0041* (2013.01); *B01D 46/0086* (2013.01); *A61L 2209/133* (2013.01); *A61L 2209/14* (2013.01);

(Continued)

(58) Field of Classification Search

CPC ........................... B01D 46/02; B01D 46/0028; B01D 46/0038; B01D 46/0041; B01D 2265/024; B01D 2265/028; B01D 2273/30; A61L 9/014; A61L 9/12; A61L 9/122; A61L 2209/10-16; F04D 29/703

See application file for complete search history.

(56) References Cited

U.S. PATENT DOCUMENTS 2,812,900 A * 11/1957 Matthews ................. F16P 1/02
416/247 R
4,102,656 A 7/1978 Koritz
(Continued)

FOREIGN PATENT DOCUMENTS

JP 2012202272 A * 10/2012
KR 20200001795 U * 8/2020 ........... F04D 29/703
KR 20220003005 U * 12/2022 ............. A47B 61/04

OTHER PUBLICATIONS

Machine translation of KR-20220003005-U (Year: 2022).*
(Continued)

*Primary Examiner* — Robert Clemente

(57) ABSTRACT

A fan cover is an apparatus designed to prevent the buildup of dust and other particles on an air fan to improve the quality of air circulating through the air fan. To do so, the apparatus comprises a cover body, an elastic band, an insert-retaining pocket, and at least one scent-modifying insert. The cover body is designed to be attached onto the air inlet of the air fan to prevent the buildup of dust and other particles on the air fan. The elastic band facilitates the secure attachment of the cover body to the air fan so that the cover body stays attached to the air fan during operation of the air fan. The insert-retaining pocket is designed to receive the at least one scent-modifying insert without obstructing the airflow through the air fan. The at least one scent-modifying insert allows the diffusion of scents and/or fragrances into the airflow.

20 Claims, 13 Drawing Sheets

(52) U.S. Cl.
CPC ..... *A61L 2209/15* (2013.01); *B01D 2265/024* (2013.01); *B01D 2265/028* (2013.01)

(56) References Cited

U.S. PATENT DOCUMENTS

| | | | | | |
|---|---|---|---|---|---|
| 4,477,272 | A * | 10/1984 | Hollis | F24F 13/28<br>D23/370 |
| 4,731,224 | A | 3/1988 | Kawashima | |
| 4,898,516 | A * | 2/1990 | Hendricks | F04D 29/703<br>416/247 R |
| 5,597,392 | A * | 1/1997 | Hawkins | F24F 13/28<br>55/DIG. 35 |
| 5,868,189 | A * | 2/1999 | Jarvis | B63H 7/02<br>150/165 |
| D408,513 | S | 4/1999 | Reede | |
| 5,904,744 | A | 5/1999 | Kagan | |
| 6,045,329 | A * | 4/2000 | Sobala | F04D 29/703<br>416/247 R |
| 2003/0188520 | A1 | 10/2003 | Boulva | |
| 2012/0224967 | A1 * | 9/2012 | Radabaugh | F04D 29/023<br>416/62 |
| 2013/0093108 | A1 | 4/2013 | Scolari | |
| 2022/0389940 | A1 * | 12/2022 | Vo | B01D 46/04 |

OTHER PUBLICATIONS

Machine translation of JP-2012202272-A (Year: 2012).*
Machine translation of KR-20200001795-U (Year: 2020).*
Fan Shroud, retrieved from the internet, retrieved on May 20, 2024; <URL: https://permatron.com/commercial_products/fan-shroud-air-filter>.
Fan Filters—Polyester—Industrial/Commercial—Box of 25, retrieved from the internet, retrieved on May 20, 2024; <URL:https://www.mymatting.com/fan-filters-polyester.html>.
Fan Shroud Filter: Fits 40 in to 42 in Fan Guard Dia., Polyester, Hook and Loop, retrieved from the internet, retrieved on May 20, 204; <URL: https://www.grainger.com/product/AIR-HANDLER-Fan-Shroud-Filter-Fits-40-2TE93>.
12 Pack of Heavy Duty Disposable Polyester Fan Shroud Air Filter, retrieved from the internet, retrieved on May 20, 2024; <URL: https://electronicaircleaners.com/fanshroudhd>.
Global Industrial™ Fan Shroud Air Filter, MERV 6, 24"W x 24"H x 6"D—Pkg Qty 12, retrieved from the internet, retrieved on May 20, 2024; <URL: https://www.globalindustrial.com/p/24-inch-fan-shroud-merv-6-air-filter-global-industrial>.

* cited by examiner

FAN COVER

The current application claims a priority to the U.S. provisional patent application Ser. No. 63/503,085 filed on May 18, 2023. The current application is filed on May 20, 2024, while May 18, 2024 was on a weekend.

FIELD OF THE INVENTION

The present invention relates generally to fan accessories and covering devices. More specifically, the present invention discloses a fan cover that can filter the airflow and diffuse scents into the airflow.

BACKGROUND OF THE INVENTION

Nowadays, air fans are widely used to generate an airflow anywhere, specially inside closed spaces. Typically, air fans include a rotating arrangement of blades that act on the air to generate the airflow. However, dust and other particles start to build up on the blades, around the inlet, and on the outlet grille of the air fan. The accumulated debris can disturb the airflow and lower the quality of air being circulated by the air fan. To prevent this, fan covers have been made available to prevent the air fan from accumulating dust or dirt. Most fan covers need to be removed when the air fan needs to be used. There are some fan covers that can be left on the air fan during operation. However, these fan covers are not reusable and fail to effectively filter the airflow generated by the air fan as well as improve air smell.

Therefore, an objective of the present invention is to provide a fan cover with air filtration and scent diffusion features. The present invention adds an extra level of filtration to fans to improve air quality. Another objective of the present invention is to prevent dirty dust-caked fan blades that affect the airflow and air quality generated by the air fan. Microorganisms can grow in the debris that causes bad smells especially in humid environments. Further, another objective of the present invention is to improve air smell by diffusing scents, such as scents from essential oils, into the air flow. Additional features and benefits of the present invention are further discussed in the sections below.

SUMMARY OF THE INVENTION

The present invention discloses a fan cover that can be attached to the inlet portion of an air fan to prevent the buildup of dust and other particles on the fan blades as well as the front and back of the fan grille. The present invention only covers the back of the air fan where the air is initially sucked in. This allows the filtration of the air flow without reducing the airflow generated by the air fan. The present invention is designed to accommodate the shape and size of the desired air fan. In addition, the present invention is designed to be left attached to the air fan even during the operation of the air fan. Further, the present invention is designed to filter the airflow to improve the quality of air circulating through the air fan. The present invention can also diffuse scents, such as scents from essential oils, into the airflow so that the air circulating is pleasant to smell.

DETAILED DESCRIPTION OF THE INVENTION

Figure 1:
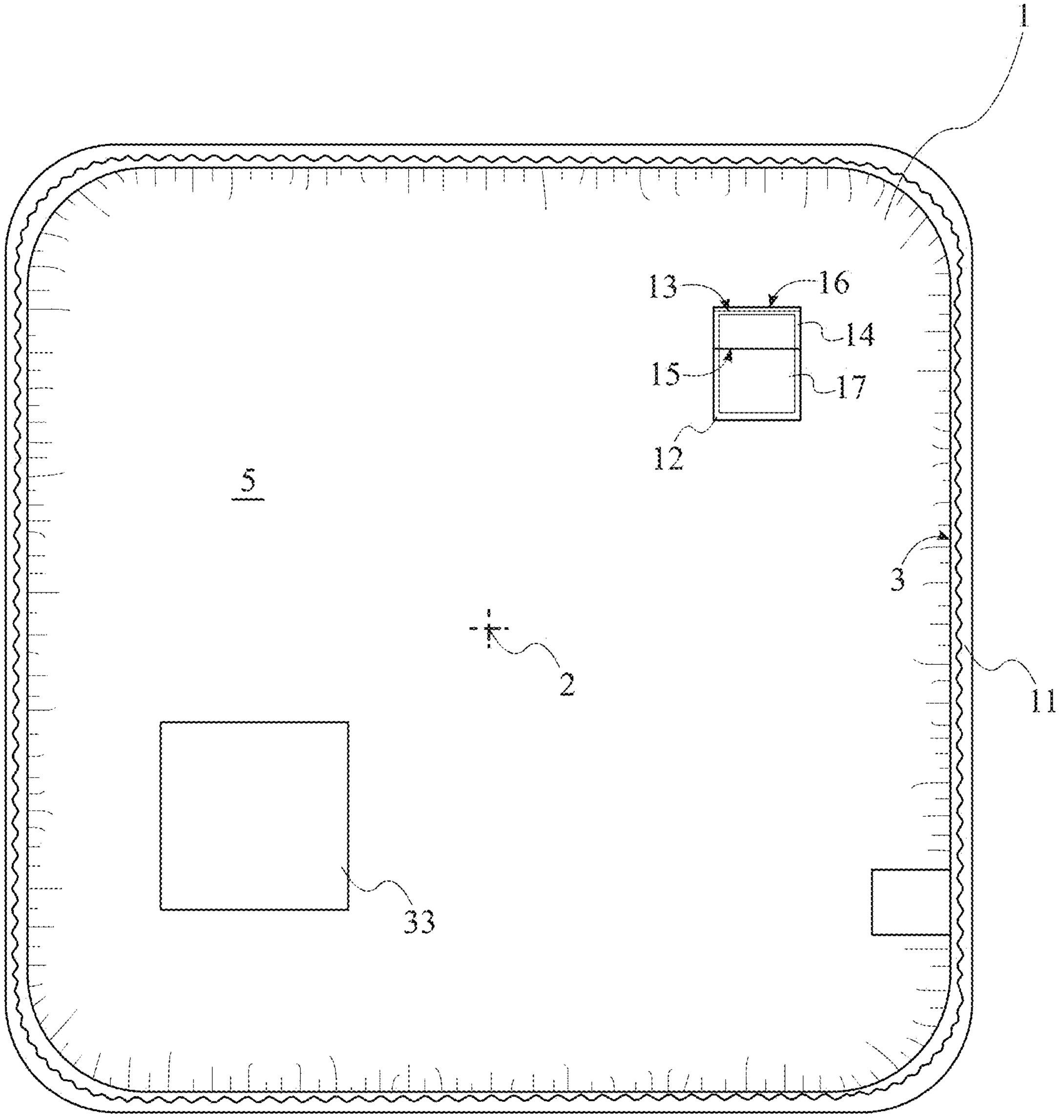
FIG. 1 is a rear-side view of the present invention, wherein the present invention is shown designed for a box fan.

All illustrations of the drawings are for the purpose of describing selected versions of the present invention and are not intended to limit the scope of the present invention.

The present invention discloses a fan cover designed to prevent the buildup of dust and other particles on an air fan to improve the quality of air circulating through the air fan. As can be seen in FIGS. 1 through 13, the present invention comprises a cover body 1, an elastic band 11, an insert-retaining pocket 12, and at least one scent-modifying insert 17. The cover body 1 is designed to be attached onto the air inlet of the air fan to significantly reduce the buildup of dust and other particles on the air fan grilles. The elastic band 11 facilitates the secure attachment of the cover body 1 to the air fan so that the cover body 1 stays attached to the air fan during operation of the air fan. The insert-retaining pocket 12 is designed to receive the at least one scent-modifying insert 17 without obstructing the airflow through the air fan. The at least one scent-modifying insert 17 allows the diffusion of scents and/or fragrances into the airflow.

The general configuration of the aforementioned components allows the air circulating through an air fan to have better quality for a more pleasant environment surrounding the air fan. As can be seen in FIGS. 1 through 13, the cover body 1 is a flexible structure that can be made from reusable, washable, and/or breathable material. For example, the cover body 1 and the insert-retaining pocket 12 are preferably made of a mesh material that allows air flow through the cover body 1. This way, when the air fan is operating, the cover body 1 filters all air flowing through the cover body 1. To do so, the cover body 1 comprises a body center 2, an outer body edge 3, a proximal face 4, and a distal face 5. The body center 2 corresponds to the center of the cover body 1, while the outer body edge 3 corresponds to the edge of the cover body 1 that forms the perimeter of the cover body 1. Further, the proximal face 4 and the distal face 5 correspond to the two opposite largest surfaces of the cover body 1 due to the thin, elongated, and flexible structure of the cover body 1.

Figure 2:
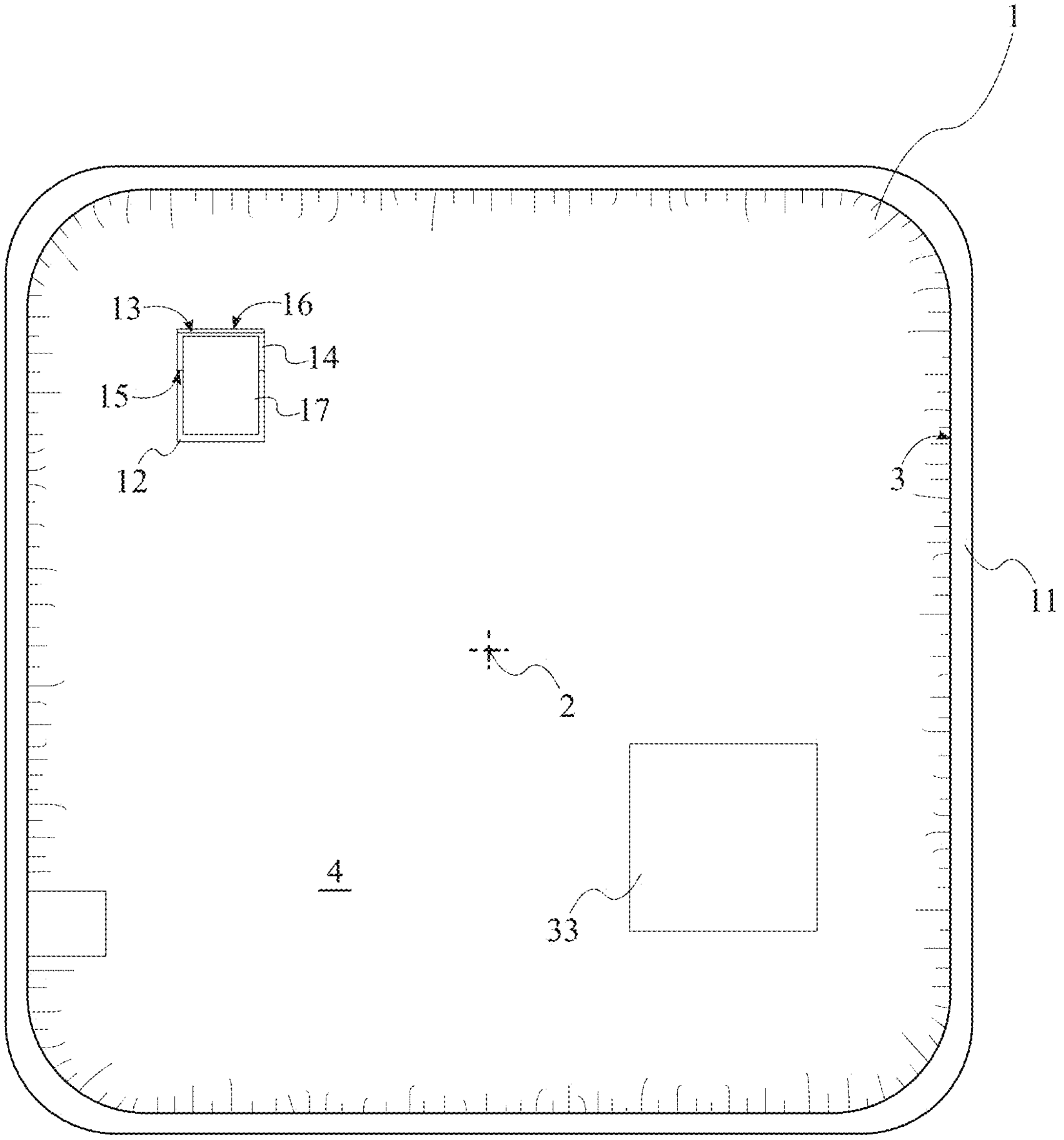
FIG. 2 is a front-side view thereof.
Figure 3:
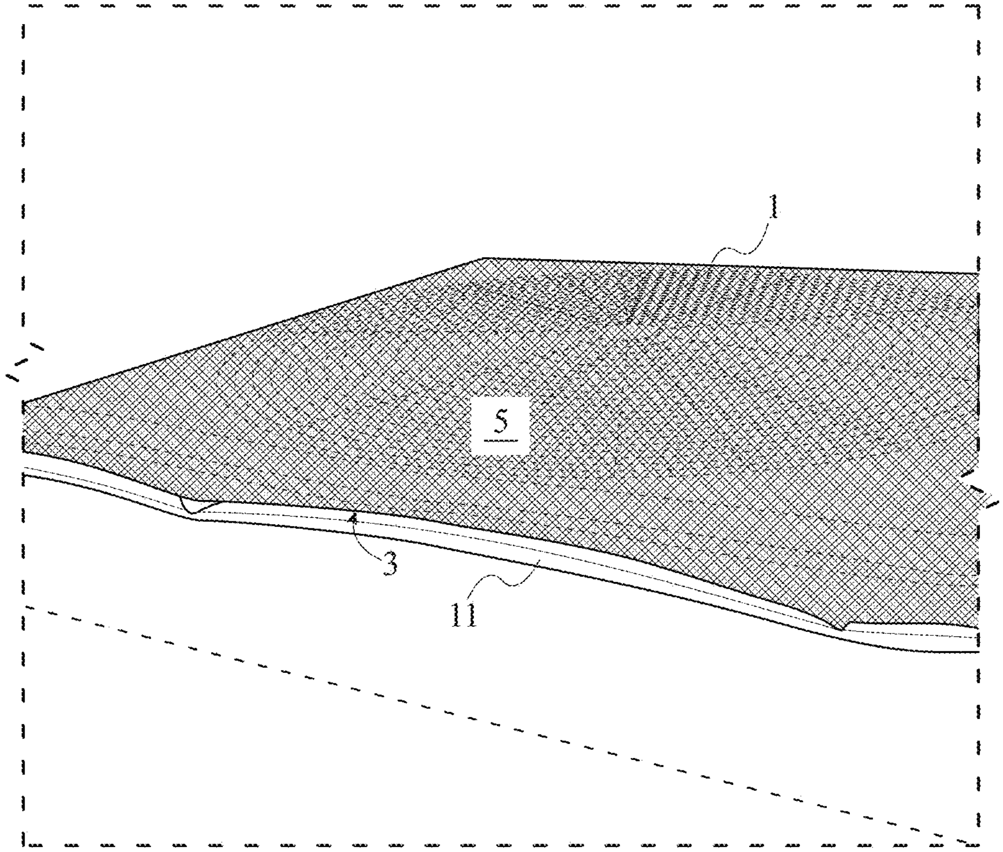
FIG. 3 is a top-perspective view thereof, wherein the present invention is shown attached to a box fan.
Figure 4:
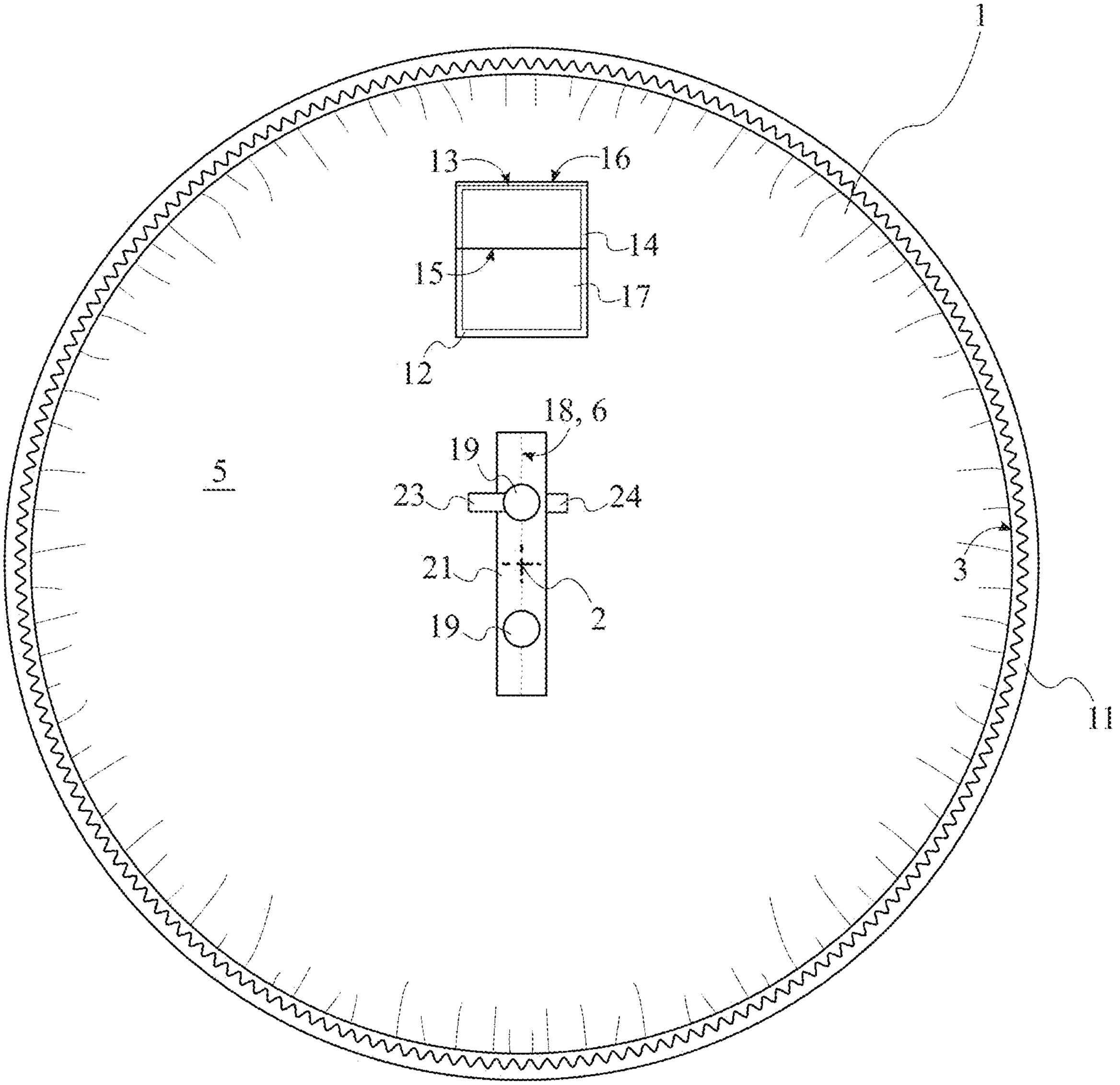
FIG. 4 is a rear-side view of the present invention, wherein the present invention is shown designed for a table fan.
Figure 5:
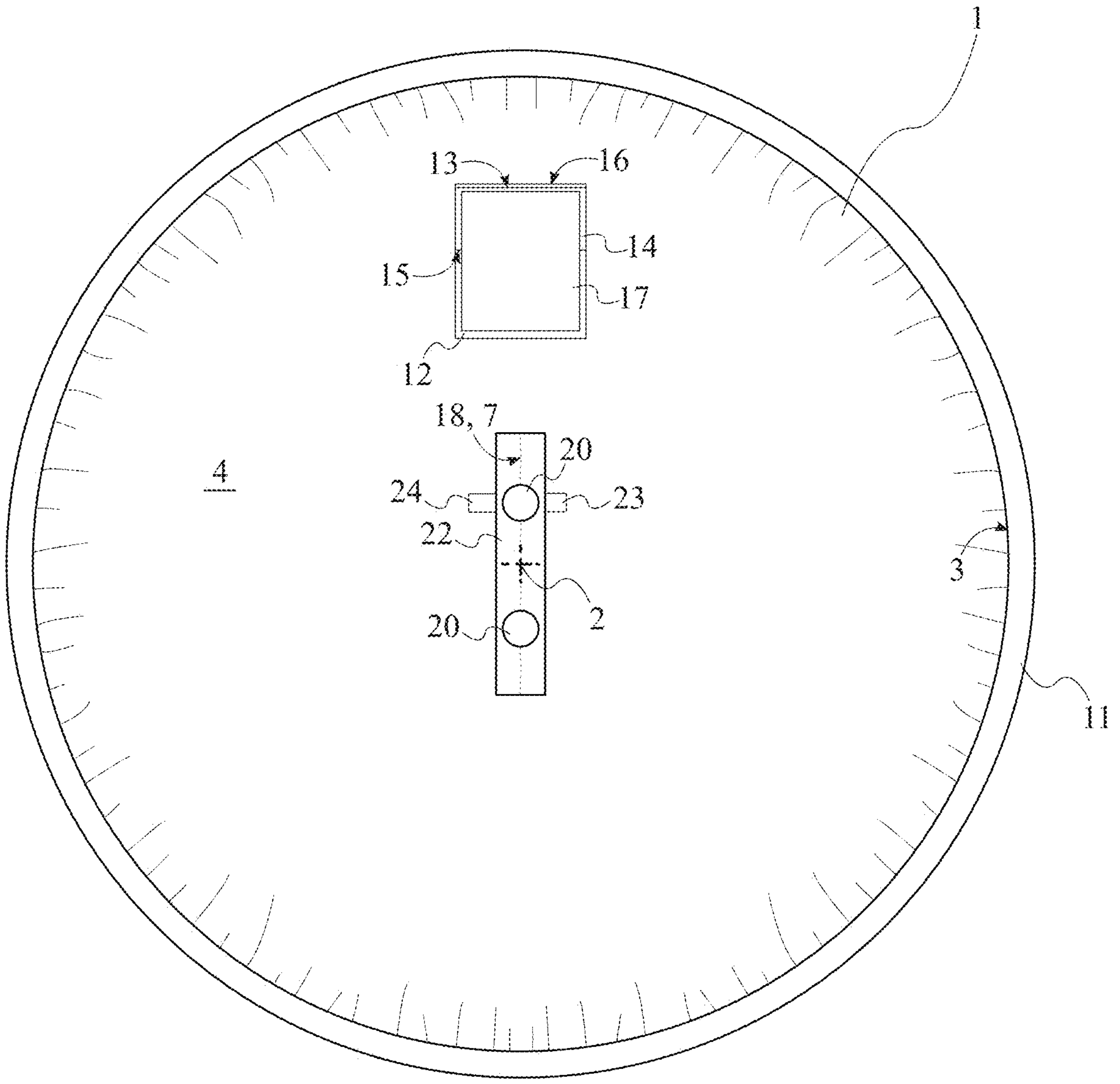
FIG. 5 is a front-side view thereof.
Figure 6:
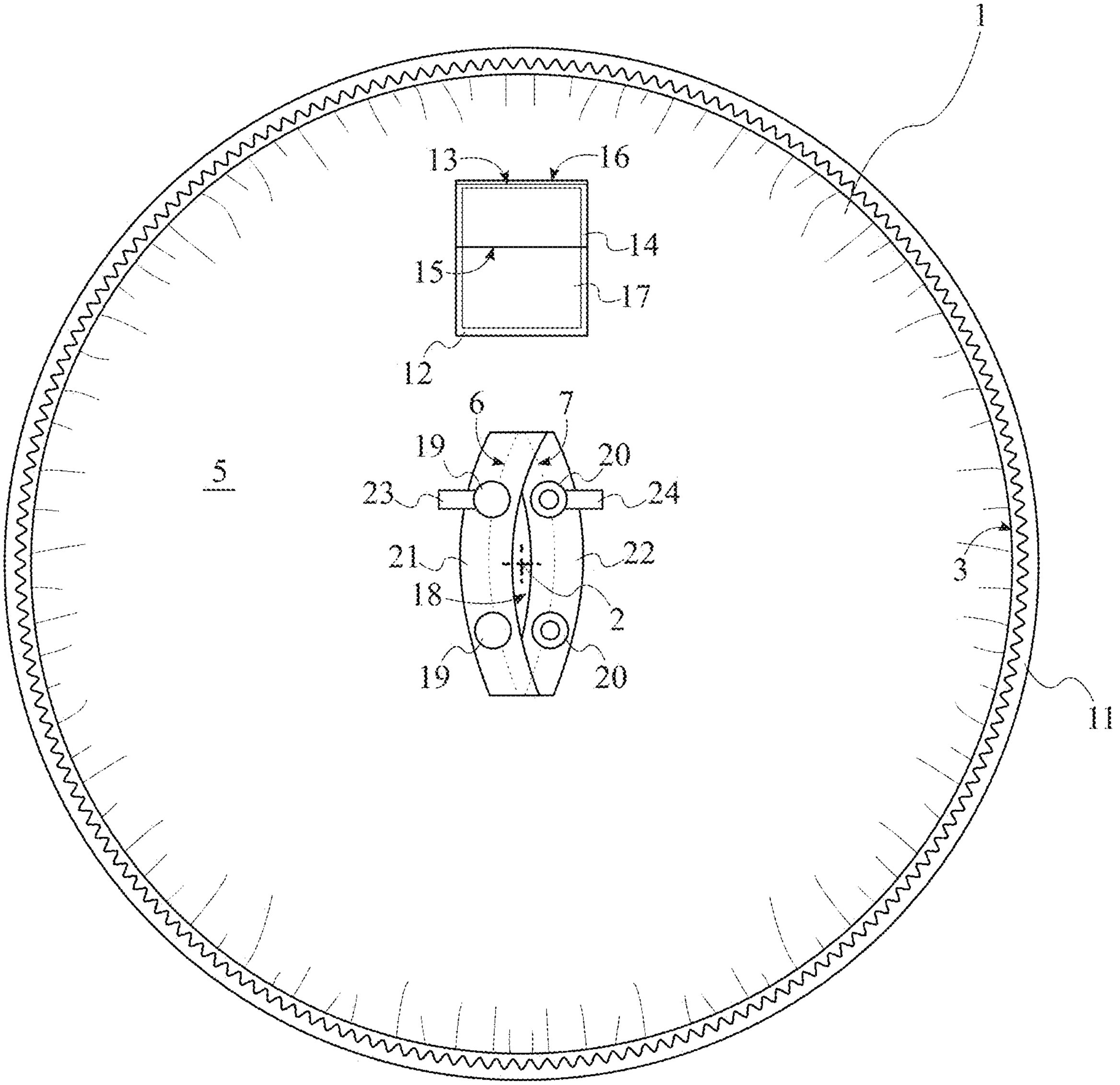
FIG. 6 is a rear-side view thereof, wherein a cover slit of the present invention is shown open.
Figure 7:
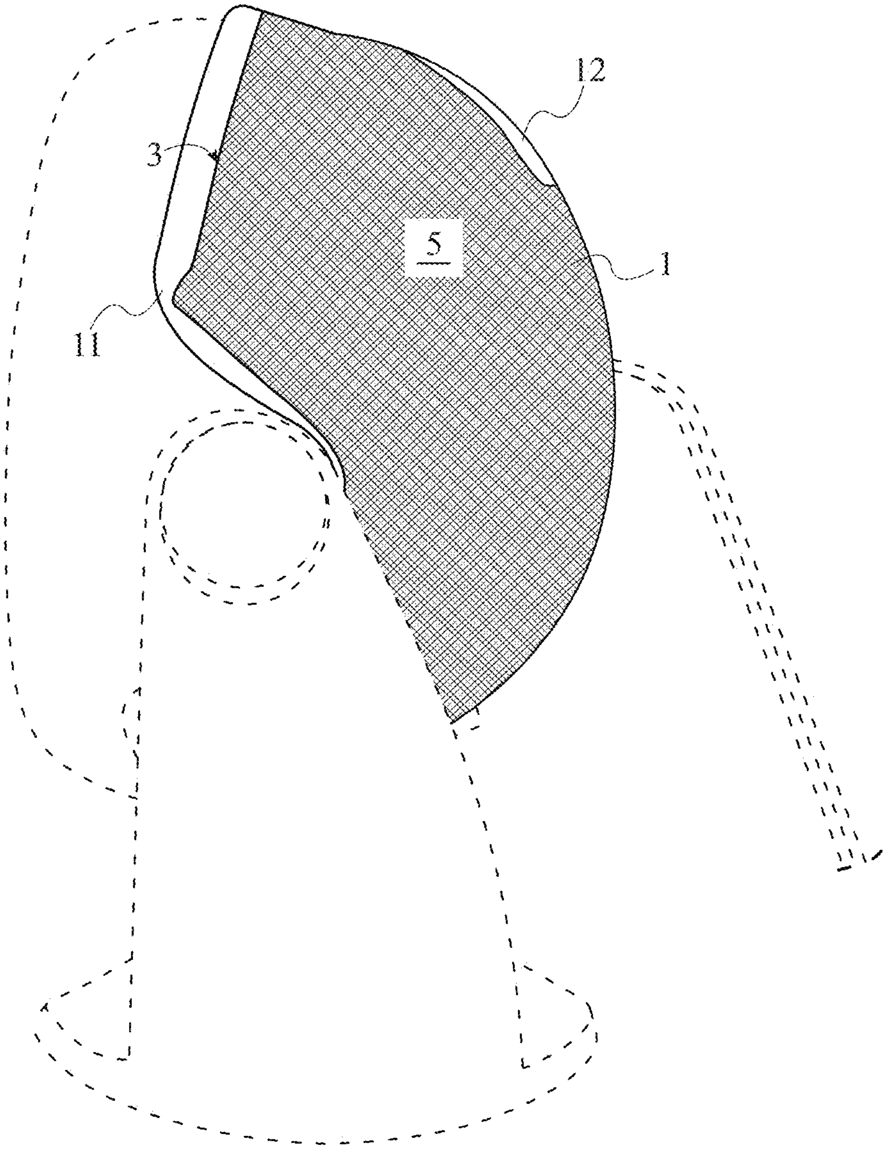
FIG. 7 is a right-side view thereof, wherein the present invention is shown attached to a table fan.
Figure 8:
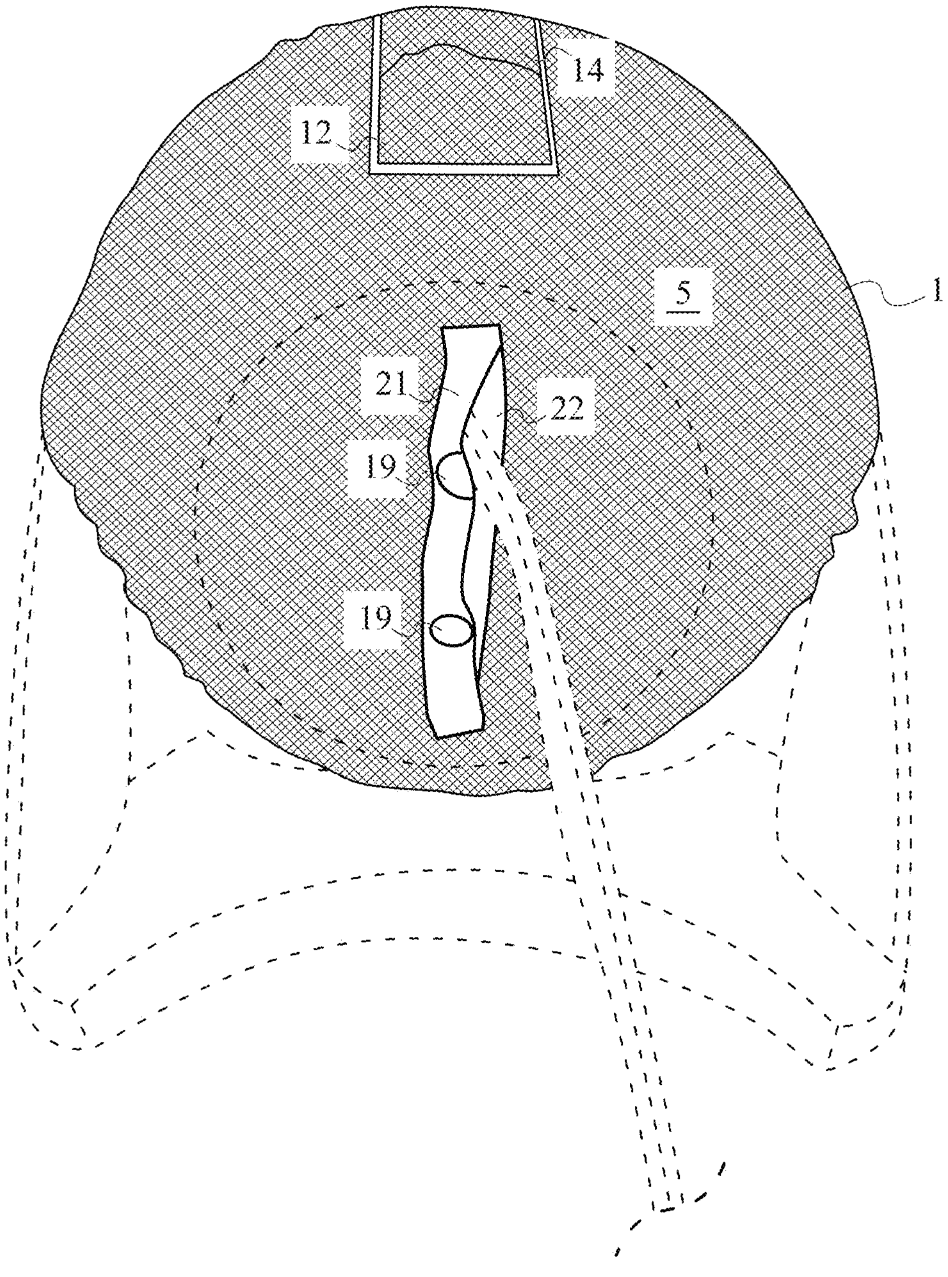
FIG. 8 is a rear-side view thereof.
Figure 9:
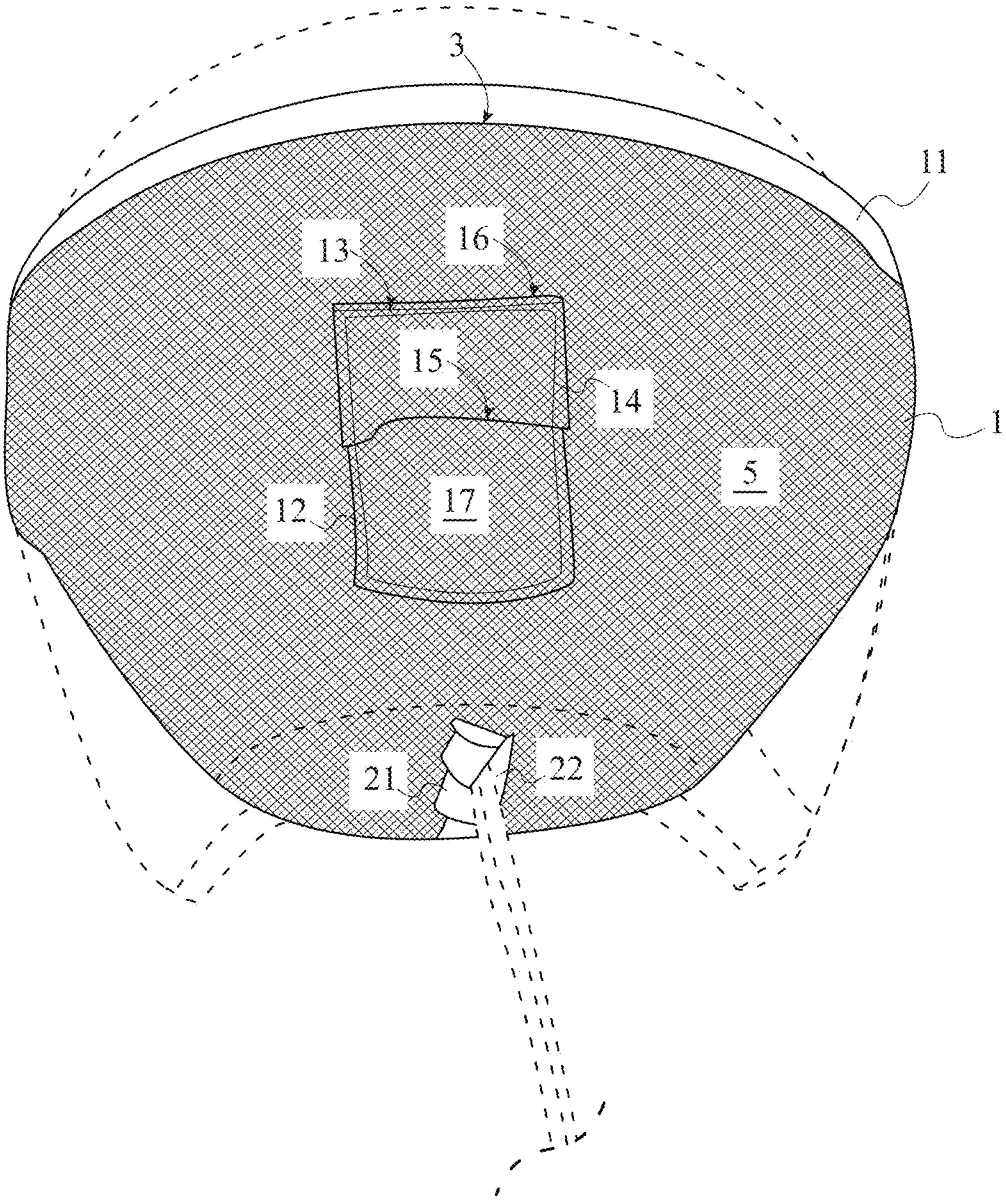
FIG. 9 is a top-side view thereof.
Figure 10:
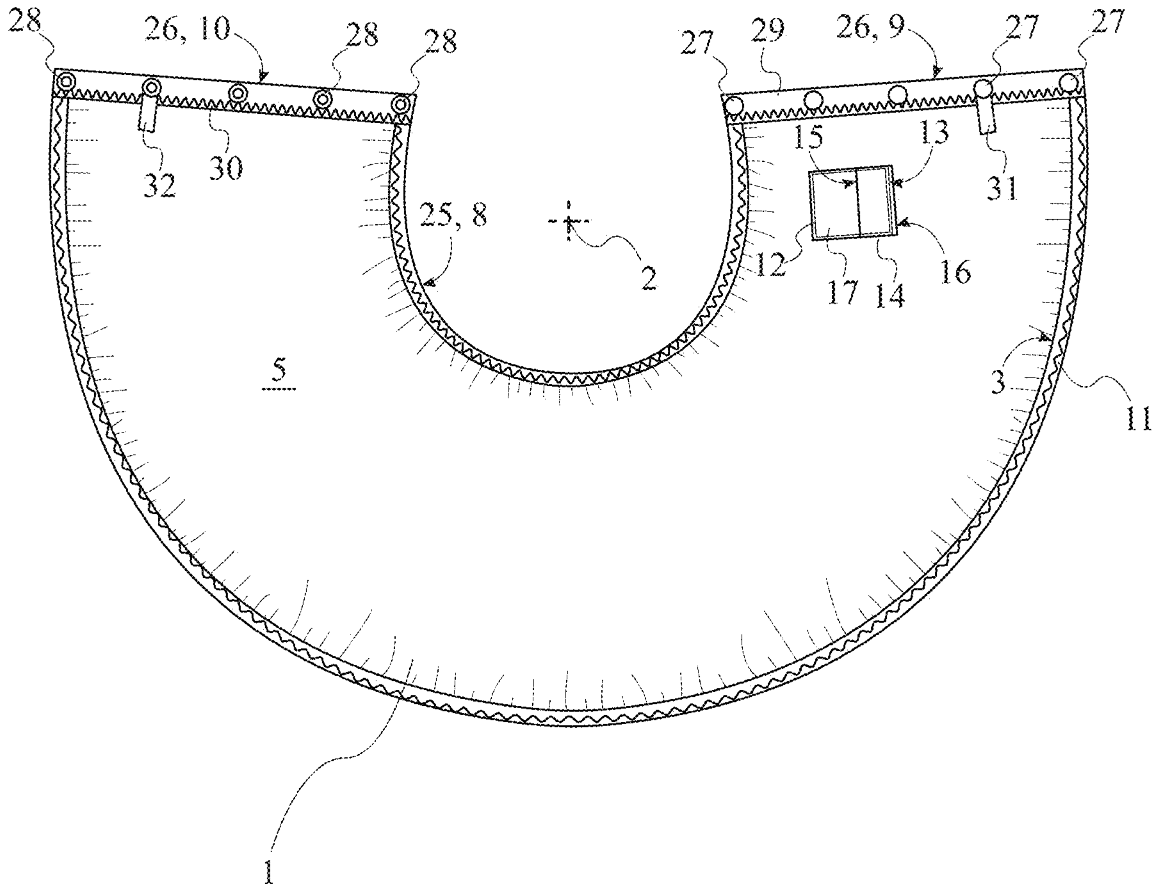
FIG. 10 is a rear-side view of the present invention, wherein the present invention is shown designed for a pedestal fan.
Figure 11:
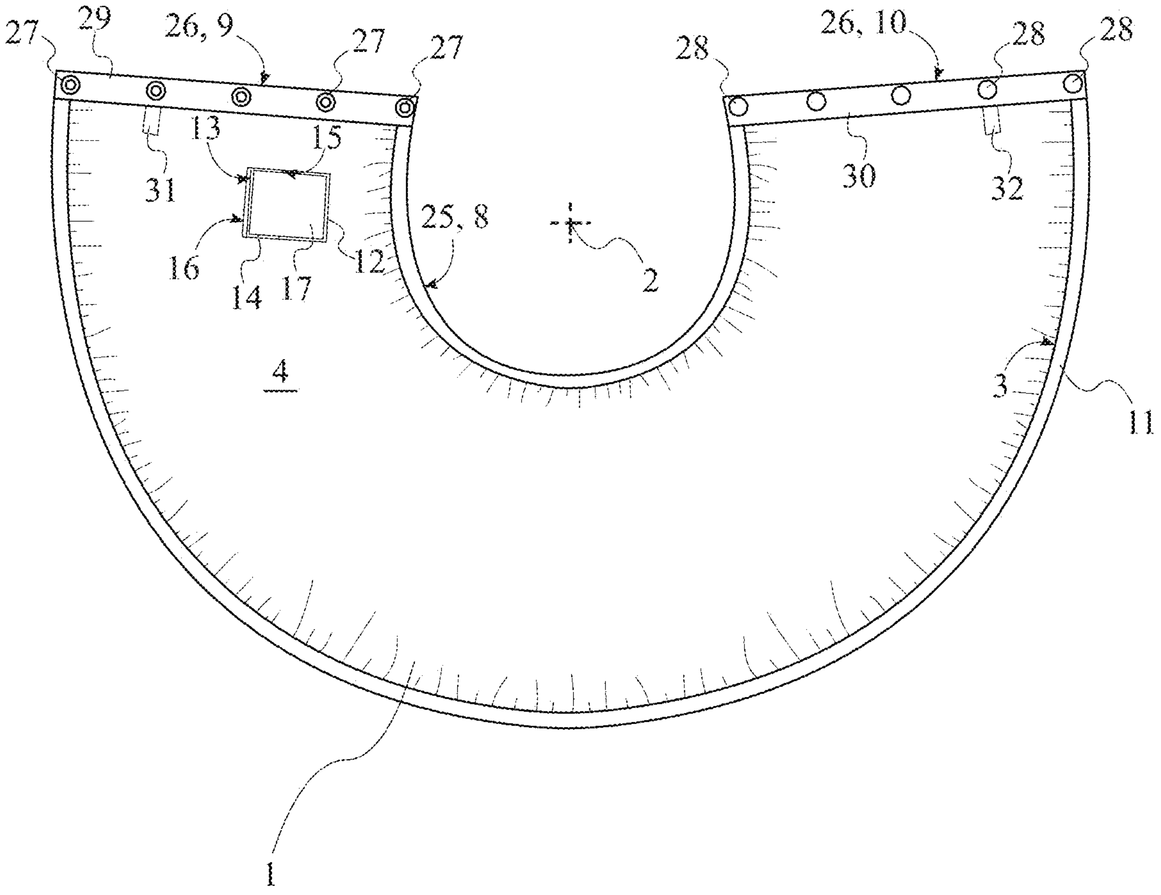
FIG. 11 is a front-side view thereof.
Figure 12:
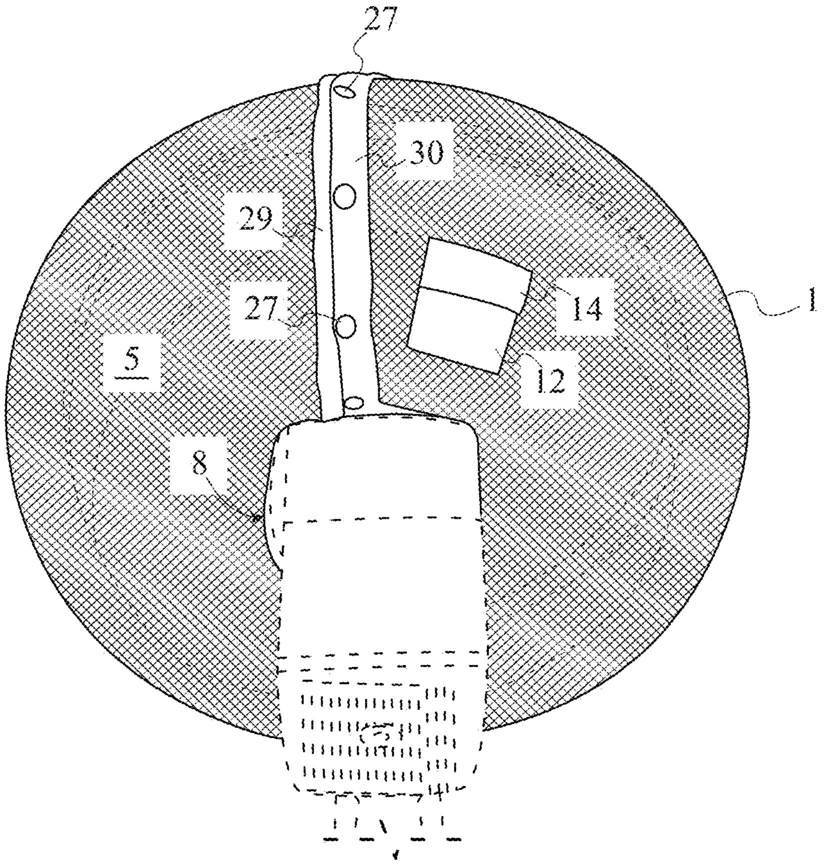
FIG. 12 is a rear-side view thereof, wherein the present invention is shown attached to a pedestal fan.
Figure 13:
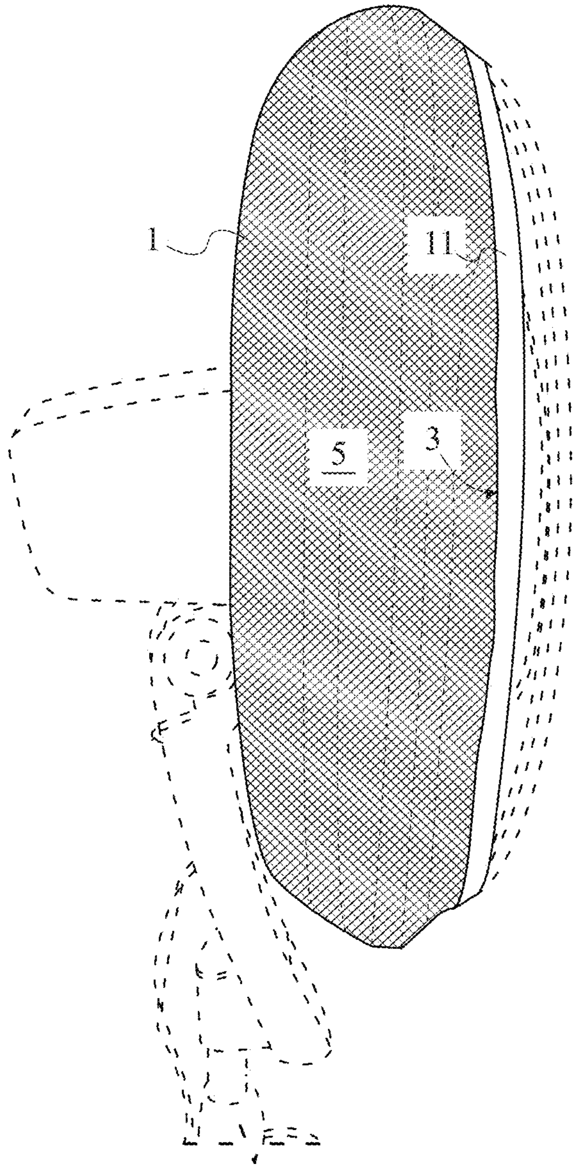
FIG. 13 is a right-side view thereof.

In addition, the cover body 1 can have different shapes that accommodate different air fan designs. As can be seen in FIGS. 1 through 3, the cover body 1 can have an overall rectangular shape that matches the design of a rectangular box fan. As can be seen in FIGS. 4 through 13, the cover body 1 can also have an overall round shape that matches the design of a table fan or a pedestal fan. Further, the cover body 1 and the insert-retaining pocket 12 can be made of a mesh material that can include 92% nylon and 8% spandex. These materials can be exchanged with other materials that are flexible and breathable. Reinforcement material can be utilized to help secure the elastic band 11 to the cover body 1 and other fasteners as needed. The reinforcement material can include 82% nylon and 18% spandex. Further, threading can be used to connect all components together, and can include 100% polyester. Furthermore, at least one scent-modifying insert 17 is preferably a cartridge-like insert that is designed to emanate odors or scents as air flows adjacent to the at least one scent-modifying insert 17. For example, the at least one scent-modifying insert 17 can be a soft pouch of porous material able to retain essential oils or other fragrances that can be diffused into the airflow circulating through the air fan. In other embodiments, different materials can be utilized for the different components of the present invention.

As can be seen in FIGS. 1 through 13, the present invention is preferably arranged as follows: the elastic band 11 is integrated along the outer body edge 3 to secure the elastic band 11 to the cover body 1. This way, the elastic band 11 forces the outer body edge 3 to close towards the body center 2 to form a cap-like structure. This way, the cover body 1 can be securely attached to the inlet portion of the air fan. Further, the insert-retaining pocket 12 is positioned in between the body center 2 and the outer body edge 3 to position the insert-retaining pocket 12 in the airflow through the air fan. Further, the insert-retaining pocket 12 is positioned offset from the body center 2 and the outer body edge 3 so that the scent from the at least one scent-modifying insert 17 is diffused into the airflow. In addition, the insert-retaining pocket 12 is connected onto the distal face 5 to secure the insert-retaining pocket 12 to the cover body 1. Furthermore, the at least one scent-modifying insert 17 is positioned within the insert-retaining pocket 12 so that the at least one scent-modifying insert 17 is kept in place inside the insert-retaining pocket 12 while the air fan is in operation.

As previously discussed, the insert-retaining pocket 12 allows the insertion of the at least one scent-modifying insert 17 in an easy manner while also keeping the at least one scent-modifying insert 17 secure inside the insert-retaining pocket 12. As can be seen in FIGS. 1 through 13, the insert-retaining pocket 12 may comprise a pocket opening 13 and a pocket flap 14. The pocket opening 13 allows the insertion and removal of the at least one scent-modifying insert 17 to/from the insert-retaining pocket 12. The pocket flap 14 is a piece of mesh material large enough to seal the pocket opening 13 to keep the at least one scent-modifying insert 17 inside the insert-retaining pocket 12. So, the pocket flap 14 may comprise a free flap edge 15 and a fixed flap edge 16 corresponding to opposite edges of the pocket flap 14. The fixed flap edge 16 is preferably the edge that is connected onto the cover body 1, while the free flap edge 15 is left unconnected to allow the insertion and removal of the at least one scent-modifying insert 17.

As can be seen in FIGS. 1 through 13, in the preferred embodiment, the insert-retaining pocket 12 can be arranged as follows: the pocket opening 13 is oriented towards the outer body edge 3 to facilitate the insertion and removal of the at least one scent-modifying insert 17. In addition, the pocket flap 14 is positioned adjacent to the pocket opening 13 so that the pocket flap 14 can seal the pocket opening 13. Further, the fixed flap edge 16 is connected onto the distal face 5 so that the pocket flap 14 is secured to the cover body 1. Furthermore, the free flap edge 15 is positioned offset to the pocket opening 13 so that the pocket flap 14 seals the pocket opening 13. In other embodiments, the insert-retaining pocket 12 can be modified to accommodate several inserts.

As previously discussed, the cover body 1 can be designed to accommodate the shape of a table fan. Most table fans have a power cord protruding from the back of the table fan, which is where the cover body 1 would be attached onto the table fan. As can be seen in FIGS. 4 through 9, to accommodate the power cord, additional wiring, or other fan features, the present invention may further comprise a cover slit 18. The cover slit 18 preferably corresponds to a narrow cut that allows the power cord and other wiring to pass through the cover body 1. To do so, the cover slit 18 traverses through the mesh body to form a cut on the cover body 1. In addition, the cover slit 18 is preferably positioned at the body center 2 to match the position of the power cord on the table fan. In other embodiments, different cuts or openings can be provided on the cover body 1 to accommodate other external fan features that may obstruct the attachment of the cover body 1 to the table fan.

Due to airflow generated by the table fan, the edges formed by the cover slit 18 may flap and cause unwanted noise while the table fan is in use. As can be seen in FIGS. 4 through 9, to prevent this, the present invention may further comprise a plurality of slit-snap caps 19 and a plurality of slit-snap sockets 20 that help seal the cover slit 18 once the cover body 1 has been attached onto the table fan. The plurality of slit-snap caps 19 and the plurality of slit-snap sockets 20 correspond to the interlocking components of several snap fasteners that help seal the cover slit 18. The plurality of slit-snap caps 19 and the plurality of slit-snap sockets 20 can be made of a plastic phosphorescent material that glows in the dark to help the user locate the table fan and the present invention in the dark. In addition, the present invention may further comprise a first slit-reinforcement strip 21 and a second slit-reinforcement strip 22 that allow for the secure connection of the plurality of slit-snap caps 19 and the plurality of slit-snap sockets 20 to the cover body 1. Further, the cover body 1 may further comprise a first slit edge 6 and a second slit edge 7 corresponding to the two edges formed by the cover slit 18.

As can be seen in FIGS. 4 through 9, the plurality of slit-snap caps 19 and the plurality of slit-snap sockets 20 can be arranged as follows: the first slit edge 6 and the second slit edge 7 are positioned opposite to each other across the cover slit 18 due to the narrow cut formed on the cover body 1 by the cover slit 18. The first slit-reinforcement strip 21 is connected along the first slit edge 6 to strengthen the first slit edge 6 with reinforcement material. In addition, the first slit-reinforcement strip 21 is positioned adjacent to the distal face 5. Likewise, the second slit-reinforcement strip 22 is connected along the second slit edge 7 to strengthen the second slit edge 7 with reinforcement material. The second slit-reinforcement strip 22 is also positioned adjacent to the distal face 5. Further, the plurality of slit-snap caps 19 is integrated along the first slit-reinforcement strip 21 to evenly distribute the plurality of slit-snap caps 19 along the first slit edge 6. Similarly, the plurality of slit-snap sockets 20 is integrated along the second slit-reinforcement strip 22 to evenly distribute the plurality of slit-snap sockets 20 along the second slit edge 7. This way, the engagement and the disengagement of the plurality of slit-snap caps 19 and the plurality of slit-snap sockets 20 does not damage the mesh material of the cover body 1. Furthermore, to seal the cover slit 18 once the cover body 1 is attached onto the table fan and the power cord is inserted through the cover slit 18, each of the plurality of slit-snap sockets 20 is selectively engaged to a corresponding socket from the plurality of slit-snap sockets 20. In other embodiments, different fastening mechanisms can be utilized to seal the cover slit 18.

As can be seen in FIGS. 4 through 9, in some embodiments, to help the user disengage the plurality of slit-snap caps 19 from the plurality of slit-snap sockets 20, the present invention may further comprise a first slit-pull tab 23 and a second slit-pull tab 24. The first slit-pull tab 23 and the second slit-pull tab 24 correspond to two short tabs that help the user disengage the plurality of slit-snap caps 19 from the plurality of slit-snap sockets 20, especially when the snap fasteners are too small for the user to easily disengage with the fingers. To do so, the first slit-pull tab 23 is connected onto the first slit-reinforcement strip 21 to secure the first slit-pull tab 23 to a slit-snap cap of the plurality of slit-snap caps 19. For example, the first slit-pull tab 23 can be riveted to a select slit-snap cap. Likewise, the second slit-pull tab 24 is connected onto the second slit-reinforcement strip 22 to secure the second slit-pull tab 24 to a slit-snap socket of the plurality of slit-snap sockets 20. The second slit-pull tab 24 can also be riveted to a select slit-snap socket. Further, the first slit-pull tab 23 and the second slit-pull tab 24 can also be made of a phosphorescent plastic material that allows the user to easily locate the first slit-pull tab 23 and the second slit-pull tab 24 in the dark. In other embodiments, additional features can be provided to help the user seal or unseal the cover slit 18 manually in an easy manner.

Similar to a table fan, a pedestal fan has several features that can prevent the easy attachment of the cover body 1 to the inlet of the pedestal fan. For example, most pedestal fans have a support column positioned on the inlet of the pedestal fan, which prevents the cover body 1 from being easily attached to the pedestal fan. As can be seen in FIGS. 10 through 13, to prevent this issue, the present invention may further comprise a cover round-cut 25 and a cover straight-cut 26. The cover round-cut 25 is designed to form a round opening on the cover body 1 that accommodates the support column of the pedestal fan. The cover straight-cut 26 allows the cover body 1 to be wrapped around the inlet of the pedestal fan for easy attachment of the cover body 1 to the pedestal fan. In addition, the cover body 1 may further comprise an inner body edge 8, a first straight edge 9, and a second straight edge 10. The inner body edge 8 is the round edge formed by the cover round-cut 25. Like the outer body edge 3, elastic band 11 can also be incorporated along the inner body edge 8 to seal the cover round-cut 25. Further, the first straight edge 9 and the second straight edge 10 corresponds to the two opposite straight edges formed by the cover straight-cut 26.

As can be seen in FIGS. 10 through 13, the embodiment of the cover body 1 for a pedestal fan can be arranged as follows: the cover round-cut 25 traverses through the cover body 1 to form the round opening that accommodates the support column of the pedestal fan. The cover round-cut 25 is also positioned at the body center 2 to match the position of the support column on the pedestal fan. Further, the inner body edge 8 is delineated by the cover round-cut 25. Similarly, the cover straight-cut 26 traverses through the cover body 1 to enable the cover body 1 to be wrapped around the inlet of the pedestal fan. Unlike the cover round-cut 25, the cover straight-cut 26 traverses from the outer body edge 3, through the inner body edge 8, and into the cover round-cut 25, to form the first straight edge 9 and the second straight edge 10. In addition, the first straight edge 9 and the second straight edge 10 are positioned opposite to each other across the cover straight-cut 26. Thus, the first straight edge 9 and the second straight edge 10 can be separated to allow the cover body 1 to be wrapped around the inlet of the pedestal fan. When the cover body 1 is laid flat, the cover body 1 will have a U-shaped structure that can be easily attached onto the pedestal fan. Once attached, the first straight edge 9 and the second straight edge 10 can be brought together to form the round structure of the cover body 1 that matches the round design of the pedestal fan. In other embodiments, different cuts and openings can be provided to accommodate other features of the pedestal fan.

As can be seen in FIGS. 10 through 13, to prevent the cover body 1 from falling off the pedestal fan once attached, the present invention may further comprise a plurality of cut-snap caps 27 and a plurality of cut-snap sockets 28. The plurality of cut-snap caps 27 and the plurality of cut-snap sockets 28 allow the detachable connection of the first straight edge 9 to the second straight edge 10 to prevent the cover body 1 from falling off the pedestal fan. The plurality of cut-snap caps 27 and the plurality of cut-snap sockets 28 correspond to the interlocking components of several snap fasteners that help connect the first straight edge 9 to the second straight edge 10. The plurality of cut-snap caps 27 and the plurality of cut-snap sockets 28 can also be made of a plastic phosphorescent material that glows in the dark to help the user locate the pedestal fan and the present invention in the dark. In addition, the present invention may further comprise a first cut-reinforcement strip 29 and a second cut-reinforcement strip 30 that help strengthen the first straight edge 9 and the second straight edge 10, respectively. The first cut-reinforcement strip 29 and the second cut-reinforcement strip 30 prevent the engagement and disengagement of the plurality of cut-snap caps 27 and the plurality of cut-snap sockets 28 from damaging the mesh material of the cover body 1.

As can be seen in FIGS. 10 through 13, the plurality of cut-snap caps 27 and the plurality of cut-snap sockets 28 can be arranged as follows: the first cut-reinforcement strip 29 is connected along the first straight edge 9 to strengthen the first straight edge 9 with reinforcement material. Similarly, the second cut-reinforcement strip 30 is connected onto the second straight edge 10 to also strengthen the second straight edge 10 with reinforcement material. Further, the plurality of cut-snap caps 27 is integrated along the first cut-reinforcement strip 29 to evenly distribute the plurality of cut-snap caps 27 along the first straight edge 9. Likewise, the plurality of cut-snap sockets 28 is integrated along the second cut-reinforcement strip 30 to evenly distribute the plurality of cut-snap sockets 28 along the second straight edge 10. Thus, when the user wants to securely connect the first straight edge 9 to the second straight edge 10, each of the plurality of cut-snap sockets 28 is selectively engaged to a corresponding socket from the plurality of cut-snap sockets 28. In other embodiments, different fastening materials can be used to selectively connect the first straight edge 9 to the second straight edge 10.

As can be seen in FIGS. 10 through 13, in some embodiments, to help the user disengage the plurality of cut-snap caps 27 from the plurality of cut-snap sockets 28, the present invention may further comprise a first cut-pull tab 31 and a second cut-pull tab 32. The first cut-pull tab 31 and the second cut-pull tab 32 correspond to two short tabs that help the user disengage the plurality of cut-snap caps 27 from the plurality of cut-snap sockets 28, especially when the snap fasteners are too small for the user to easily disengage with the fingers. To do so, the first cut-pull tab 31 is connected onto the first cut-reinforcement strip 29 to secure the first cut-pull tab 31 to a cut-snap cap of the plurality of cut-pull caps. For example, the first cut-pull tab 31 can be riveted to a select cut-snap cap. Likewise, the second cut-pull tab 32 is connected onto the second cut-reinforcement strip 30 to secure the second cut-pull tab 32 to a cut-snap socket of the plurality of cut-snap sockets 28. The second cut-pull tab 32 can also be riveted to a select cut-snap socket. Further, the first cut-pull tab 31 and the second cut-pull tab 32 can also be made of a phosphorescent plastic material that allows the user to easily locate the first cut-pull tab 31 and the second cut-pull tab 32 in the dark. In other embodiments, additional features can be provided to help the user connect or disconnect the first straight edge 9 and the second straight edge 10 manually.

In some embodiments, the present invention can include various features that help the user properly maintain the present invention in order to have proper filtration of the airflow through the air fan and maintain good air quality. For example, the present invention may include a care label that is terminally attached to the cover body 1 to provide the user with care instructions. The care instructions can include information regarding the materials of the present invention as well as the proper cleaning method of the present invention that does not damage the cover body 1 or the other components. Further, the present invention may include means to indicate to the user when maintenance is necessary for the present invention. As can be seen in FIGS. 1 and 2, the present invention may further comprise a fabric wash indicator 33 that visually indicates the user when the user should wash the present invention. The fabric wash indicator 33 can be a chemically activated patch that changes color once a predetermined amount of dirt and other particles accumulate on the fabric wash indicator 33. Further, the fabric wash indicator 33 is mounted onto the distal face 5 to secure the fabric wash indicator 33 to the cover body 1. In other embodiments, different indicators can be implemented to help the user monitor the condition of the components of the present invention to ensure the best quality of air in the surroundings of the air fan.

Although the invention has been explained in relation to its preferred embodiment, it is to be understood that many other possible modifications and variations can be made without departing from the spirit and scope of the invention.

What is claimed is:

1. A fan cover comprising:
a cover body;
an elastic band;
an insert-retaining pocket;
at least one scent-modifying insert;
the cover body comprising a body center, an outer body edge, a proximal face, and a distal face;
the cover body and the insert-retaining pocket being made of a mesh material;
the elastic band being integrated along the outer body edge;
the insert-retaining pocket being positioned in between the body center and the outer body edge;
the insert-retaining pocket being positioned offset from the body center and the outer body edge;
the insert-retaining pocket being connected onto the distal face; and
the at least one scent-modifying insert being positioned within the insert-retaining pocket.

2. The fan cover as claimed in claim 1 further comprising:
the insert-retaining pocket comprising a pocket opening and a pocket flap;
the pocket flap comprising a free flap edge and a fixed flap edge;
the pocket opening being oriented towards the outer body edge;
the pocket flap being positioned adjacent to the pocket opening;
the fixed flap edge being connected onto the distal face; and
the free flap edge being positioned offset to the pocket opening.

3. The fan cover as claimed in claim 1 further comprising:
a cover slit;
the cover slit traversing through the mesh body; and
the cover slit being positioned at the body center.

4. The fan cover as claimed in claim 3 further comprising:
a plurality of slit-snap caps;
a plurality of slit-snap sockets;
a first slit-reinforcement strip;
a second slit-reinforcement strip;
the cover body further comprising a first slit edge and a second slit edge;
the first slit edge and the second slit edge being positioned opposite to each other across the cover slit;
the first slit-reinforcement strip being connected along the first slit edge;
the first slit-reinforcement strip being positioned adjacent to the distal face;
the second slit-reinforcement strip being connected along the second slit edge;
the second slit-reinforcement strip being positioned adjacent to the distal face;
the plurality of slit-snap caps being integrated along the first slit-reinforcement strip;
the plurality of slit-snap sockets being integrated along the second slit-reinforcement strip; and
each of the plurality of slit-snap sockets being selectively engaged to a corresponding socket from the plurality of slit-snap sockets.

5. The fan cover as claimed in claim 4, wherein the plurality of first snap caps and the plurality of first snap sockets are made of a phosphorescent material.

6. The fan cover as claimed in claim 4 further comprising:
a first slit-pull tab;
a second slit-pull tab;
the first slit-pull tab being connected onto the first slit-reinforcement strip; and
the second slit-pull tab being connected onto the second slit-reinforcement strip.

7. The fan cover as claimed in claim 6, wherein the first slit-pull tab and the second slit-pull tab are made of a phosphorescent material.

8. The fan cover as claimed in claim 1 further comprising:
a cover round-cut;
a cover straight-cut;
the cover body further comprising an inner body edge, a first straight edge, and a second straight edge;
the cover round-cut traversing through the cover body;
the cover round-cut being positioned at the body center;
the inner body edge being delineated by the cover round-cut;
the cover straight-cut traversing through the cover body;
the cover straight-cut traversing from the outer body edge, through the inner body edge, and into the cover round-cut; and
the first straight edge and the second straight edge being positioned opposite to each other across the cover straight-cut.

9. The fan cover as claimed in claim 8 further comprising:
a plurality of cut-snap caps;

a plurality of cut-snap sockets;
a first cut-reinforcement strip;
a second cut-reinforcement strip;
the first cut-reinforcement strip being connected along the first straight edge;
the second cut-reinforcement strip being connected onto the second straight edge;
the plurality of cut-snap caps being integrated along the first cut-reinforcement strip;
the plurality of cut-snap sockets being integrated along the second cut-reinforcement strip; and
each of the plurality of cut-snap sockets being selectively engaged to a corresponding socket from the plurality of cut-snap sockets.

10. The fan cover as claimed in claim 9, wherein the plurality of cut-snap caps and the plurality of cut-snap sockets are made of a phosphorescent material.

11. The fan cover as claimed in claim 9 further comprising:
a first cut-pull tab;
a second cut-pull tab;
the first cut-pull tab being connected onto the first cut-reinforcement strip; and
the second cut-pull tab being connected onto the second cut-reinforcement strip.

12. The fan cover as claimed in claim 11, wherein the first cut-pull tab and the second cut-pull tab are made of a phosphorescent material.

13. The fan cover as claimed in claim 1, wherein the cover body is made of a silver-impregnated antimicrobial mesh fabric.

14. The fan cover as claimed in claim 1, wherein the insert-retaining pocket is made of a silver-impregnated antimicrobial mesh fabric.

15. The fan cover as claimed in claim 1 further comprising:
a fabric wash indicator; and
the fabric wash indicator being mounted onto the distal face.

16. A fan cover comprising:
a cover body;
an elastic band;
an insert-retaining pocket;
at least one scent-modifying insert;
a fabric wash indicator;
the cover body comprising a body center, an outer body edge, a proximal face, and a distal face;
the insert-retaining pocket comprising a pocket opening and a pocket flap;
the pocket flap comprising a free flap edge and a fixed flap edge;
the cover body and the insert-retaining pocket being made of a silver-impregnated antimicrobial mesh fabric;
the elastic band being integrated along the outer body edge;
the insert-retaining pocket being positioned in between the body center and the outer body edge;
the insert-retaining pocket being positioned offset from the body center and the outer body edge;
the insert-retaining pocket being connected onto the distal face;
the at least one scent-modifying insert being positioned within the insert-retaining pocket;
the pocket opening being oriented towards the outer body edge;
the pocket flap being positioned adjacent to the pocket opening;
the fixed flap edge being connected onto the distal face;
the free flap edge being positioned offset to the pocket opening; and
the fabric wash indicator being mounted onto the distal face.

17. The fan cover as claimed in claim 16 further comprising:
a cover slit;
a plurality of slit-snap caps;
a plurality of slit-snap sockets;
a first slit-reinforcement strip;
a second slit-reinforcement strip;
a first slit-pull tab;
a second slit-pull tab;
the cover body further comprising a first slit edge and a second slit edge;
the cover slit traversing through the mesh body;
the cover slit being positioned at the body center;
the first slit edge and the second slit edge being positioned opposite to each other across the cover slit;
the first slit-reinforcement strip being connected along the first slit edge;
the first slit-reinforcement strip being positioned adjacent to the distal face;
the second slit-reinforcement strip being connected along the second slit edge;
the second slit-reinforcement strip being positioned adjacent to the distal face;
the plurality of slit-snap caps being integrated along the first slit-reinforcement strip;
the plurality of slit-snap sockets being integrated along the second slit-reinforcement strip;
each of the plurality of slit-snap sockets being selectively engaged to a corresponding socket from the plurality of slit-snap sockets;
the first slit-pull tab being connected onto the first slit-reinforcement strip; and
the second slit-pull tab being connected onto the second slit-reinforcement strip.

18. The fan cover as claimed in claim 17, wherein the plurality of first snap caps, the plurality of first snap sockets, the first slit-pull tab, and the second slit-pull tab are made of a phosphorescent material.

19. The fan cover as claimed in claim 16 further comprising:
a cover round-cut;
a cover straight-cut;
a plurality of cut-snap caps;
a plurality of cut-snap sockets;
a first cut-reinforcement strip;
a second cut-reinforcement strip;
a first cut-pull tab;
a second cut-pull tab;
the cover body further comprising an inner body edge, a first straight edge, and a second straight edge;
the cover round-cut traversing through the cover body;
the cover round-cut being positioned at the body center;
the inner body edge being delineated by the cover round-cut;
the cover straight-cut traversing through the cover body;
the cover straight-cut traversing from the outer body edge, through the inner body edge, and into the cover round-cut;
the first straight edge and the second straight edge being positioned opposite to each other across the cover straight-cut;

the first cut-reinforcement strip being connected along the first straight edge;

the second cut-reinforcement strip being connected onto the second straight edge;

the plurality of cut-snap caps being integrated along the first cut-reinforcement strip;

the plurality of cut-snap sockets being integrated along the second cut-reinforcement strip;

each of the plurality of cut-snap sockets being selectively engaged to a corresponding socket from the plurality of cut-snap sockets;

the first cut-pull tab being connected onto the first cut-reinforcement strip; and the second cut-pull tab being connected onto the second cut-reinforcement strip.

20. The fan cover as claimed in claim 19, wherein the plurality of cut-snap caps, the plurality of cut-snap sockets, the first cut-pull tab, and the second cut-pull tab are made of a phosphorescent material.

* * * * *